(12) United States Patent
Eggen et al.

(10) Patent No.: US 10,898,707 B2
(45) Date of Patent: Jan. 26, 2021

(54) SECURING AN IMPLANTABLE MEDICAL DEVICE IN POSITION WHILE REDUCING PERFORATIONS

(71) Applicant: MEDTRONIC, INC., Minneapolis, MN (US)

(72) Inventors: Michael D. Eggen, Chisago City, MN (US); Kevin R. Seifert, Forest Lake, MN (US); Vladimir Grubac, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 105 days.

(21) Appl. No.: 16/184,596

(22) Filed: Nov. 8, 2018

(65) Prior Publication Data

US 2019/0076646 A1 Mar. 14, 2019

Related U.S. Application Data

(62) Division of application No. 15/153,914, filed on May 13, 2016, now Pat. No. 10,143,838.

(Continued)

(51) Int. Cl.
*A61N 1/05* (2006.01)

(52) U.S. Cl.
CPC ........... *A61N 1/0573* (2013.01); *A61N 1/059* (2013.01)

(58) Field of Classification Search
None
See application file for complete search history.

(56) References Cited

U.S. PATENT DOCUMENTS

| 4,103,690 A | 8/1978 | Harris |
| 4,505,767 A | 3/1985 | Quin |

(Continued)

FOREIGN PATENT DOCUMENTS

| CN | 103249454 A | 8/2013 |
| CN | 103561810 A | 2/2014 |
| CN | 103635160 A | 3/2014 |

OTHER PUBLICATIONS

Eggen et al, Design and Evaluation of a Novel Fixation Mechanism for a Transcatheter Pacemaker, IEEE Transactions on Biomedical Engineering, vol. 62, No. 9, (Sep. 9, 2015), 8 pages.

(Continued)

*Primary Examiner* — Brian T Gedeon

(57) ABSTRACT

Methods and systems of making a medical electrical lead type having a set of tines. A system for implantation of a lead medical electrical lead in contact with heart tissue, comprises an elongated lead body; a set of curved tines mounted to and extending from a distal end of the lead body, the tines having a length (dD) and an effective cross sectional area, and a delivery catheter. The delivery catheter encloses the lead body and has a distal capsule portion enclosing the tines. The tines exerting a spring force against the capsule and provide a stored potential energy. The delivery catheter has an elastic, not stiff and low column strength ejection means for advancing the lead and tines distally from the capsule and fixating the tines within the heart tissue, the controllable and the stored potential energy of the tines together provide a deployment energy. The tines when so fixated in the tissue provide a fixation energy. The deployment energy and the fixation energy of the tines are equivalent.

31 Claims, 12 Drawing Sheets

Related U.S. Application Data

(60) Provisional application No. 62/160,710, filed on May 13, 2015.

(56) References Cited

U.S. PATENT DOCUMENTS

| | | | |
|---|---|---|---|
| 5,067,957 | A | 11/1991 | Jervis |
| 7,601,033 | B2 | 10/2009 | Ries et al. |
| 7,650,186 | B2 | 1/2010 | Hastings et al. |
| 7,654,843 | B2 | 2/2010 | Olson et al. |
| 7,783,365 | B2 | 8/2010 | Ebert et al. |
| 8,005,549 | B2 | 8/2011 | Boser et al. |
| 9,526,891 | B2 | 12/2016 | Eggen et al. |
| 9,675,798 | B2 | 6/2017 | Grubac et al. |
| 9,775,982 | B2 | 10/2017 | Grubac et al. |
| 2012/0172892 | A1* | 7/2012 | Grubac .............. A61N 1/05 606/129 |
| 2013/0138136 | A1 | 5/2013 | Beckham et al. |
| 2014/0005762 | A1 | 1/2014 | Wu et al. |
| 2015/0039071 | A1 | 2/2015 | Grubac et al. |
| 2015/0045868 | A1 | 2/2015 | Bonner et al. |
| 2016/0059003 | A1 | 3/2016 | Eggen et al. |

OTHER PUBLICATIONS

Medtronic, Inc., Manual for the CAPSURE SENSE® 4074, 8 pages.
St. Jude Medical Manual, ISLOFLEX™, 2 pages.
Boston Scientific Inv., Manual for INGEVITY™ MRI lead, 1 page.
(PCT/US2016/032308) PCT Notification of Transmittal of the International Search Report and the Written Opinion of the International Searching Authority, dated Jul. 20, 2016, 11 pages.

\* cited by examiner

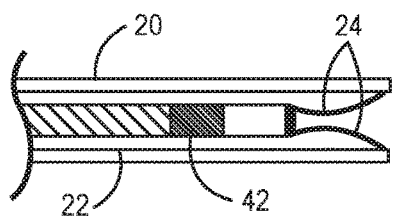
FIG. 11A
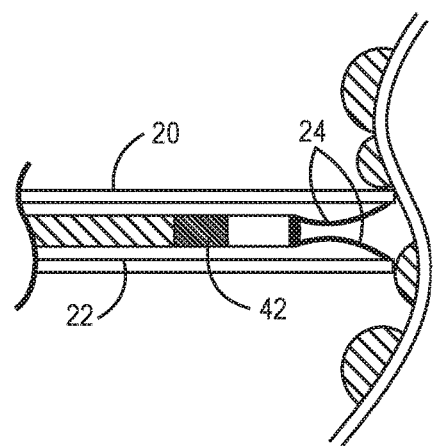
FIG. 11B
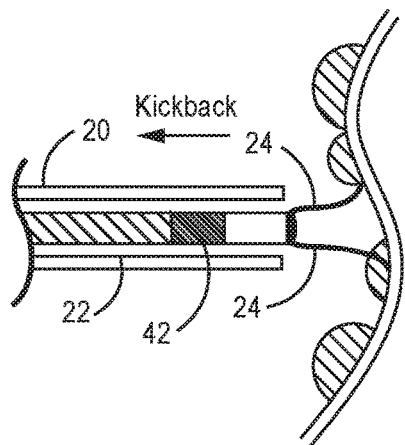
FIG. 11D
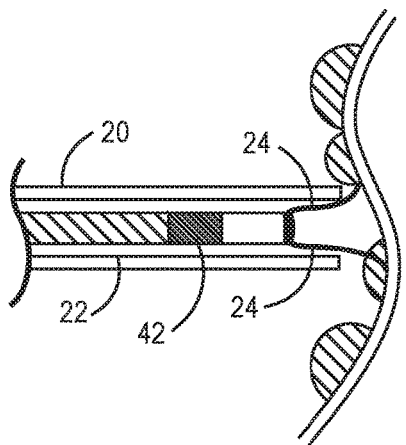
FIG. 11C
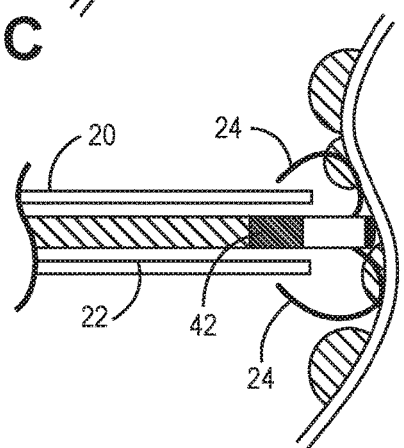
FIG. 11E

SECURING AN IMPLANTABLE MEDICAL DEVICE IN POSITION WHILE REDUCING PERFORATIONS

CROSS-REFERENCE TO RELATED APPLICATIONS

This application claims the benefit of U.S. Provisional Application No. 62/160,710, filed on May 13, 2015. The disclosure of the above application is incorporated herein by reference in its entirety.

TECHNICAL FIELD

This disclosure relates to implantable medical devices such as medical electrical leads. More particularly, the present disclosure relates to a medical electrical lead with a set of tines that are configured to securely attach to tissue without perforating the heart wall.

BACKGROUND

Medical electrical leads are configured for pacing, sensing, cardioversion, and defibrillation therapies. Leads attach to tissue through active fixation (e.g. tines etc.) or passive fixation (e.g. adhesive). Exemplary medical electrical devices with tines, comprising nickel titanium (Nitinol), are known in the art, as shown and described in U.S. Pat. No. 4,505,767 to Quinn, U.S. Pat. No. 5,067,957 to Jervis, U.S. Pat. No. 7,650,186 to Hastings et al. and US Pregrant Publication No. 2012-0172892 A1 filed Apr. 28, 2011 to Grubac et al. Delivery of therapy is dependent upon the lead tines staying attached to the cardiac tissue. Occasionally, a lead can dislodge from its position which is problematic since therapy cannot be delivered to the tissue. Lead tines can be designed to be securely attached to tissue in a manner that the lead will not dislodge; however, perforations of the heart wall can increase. Perforations occur when tines completely pierce or penetrate the heart wall that comprises three layers—endocardium, myocardium and epicardium. Each heart wall layer possesses different tissue properties. For example, the epicardium is harder than the thicker softer myocardium while the myocardium is softer than the endocardium. Since each heart wall layer possesses different tissue properties, tines pass through each layer at a different rate of speed. Consequently, reduced dislodgement of tines must be balanced against reduction of perforations by tines.

Typically, to address this issue, lead tines have been designed based upon a push force applied by user that is translated to the tines. It is desirable to develop tines, on a medical device, that does not merely rely on the force applied by the tines but rather eliminates dislodgement while substantially reducing perforations during implanting of a medical device.

SUMMARY

The present disclosure is directed to a medical electrical lead having set of tines that eliminates unintended dislodgements from tissue. Energy stored in the tines is released when the delivery system is retracted. Retracting the delivery system controls the penetration of the set of tines into the cardiac tissue (i.e. myocardium).

The set of tines are configured to satisfy pre-specified conditions. For example, tines must be easily deployed and attached to various types of cardiac tissue (e.g. endocardium, myocardium and epicardium) while ensuring adequate fixation occurs to avoid dislodgment of the tines from the tissue. Additionally, the tines are required to hold the electrode in contact with the myocardium to maintain low stable pacing thresholds. Moreover, the tines must be able to be easily removed with minimal damage to the myocardium, in order to facilitate device repositioning, retrieval and extraction. Device repositioning typically occurs to achieve a more optimal pacing location. Retrieval and extraction may occur when a healthcare professional (e.g. physician) determines that the implantable medical device (IMD) needs to be replaced with another IMD.

One or more embodiments relate to configuring a crown with a set of tines extending therefrom in which the crown is secured (e.g. snap-fit, adhesive) to any medical electrical lead. The set of tines are configured by using a set of transfer functions. The first transfer function is directed to tissue penetration by the tines. The tissue penetration transfer function relates an effective cross-sectional area of the fixation mechanism (e.g. fixated tine etc.) at retraction to the effective cross-sectional area of the fixation mechanism (e.g. tine etc.) at the point of deployment of the tine(s). Specifically, the effective cross-sectional area of the fixation mechanism (e.g. fixated tine etc.) at retraction is configured to be larger than the effective cross-sectional area of the fixation mechanism (e.g. tine etc.) at the point of deployment of the tine(s).

The second transfer function configures tines in a manner that allows the tines to be safely removed from the myocardium. To ensure the tines can be safely removed, the second transfer function relates penetration energy and surface area. The tissue penetration energy at a surface area equivalent to the inside surface area $48a$ of the tine (FIG. 8) compared to the holding energy of the tines upon retraction to determine if the tines would damage tissue upon retraction. Holding energy (WintgR) is deployment work/energy of the retraction portion of a full cycle test.

The second transfer function associates maximum peak force of deployment and retraction to occur at substantially equivalent displacements of the tine cycle. A full tine cycle is shown from FIGS. 3A-3D in which the tines enter and attach to cardiac tissue.

One or more other embodiments relates to a method of making a medical electrical lead type having a set of tines. The method comprises determining an effective cross-sectional area characteristic of a distal end of each tine in the set of tines relative to a displacement energy required to displace a cardiac tissue layers. In response to determining the effective cross-sectional area characteristic of the distal end of each tine, a determination is made as to whether a substantially high confidence level (e.g. 95% or more) characteristic exists that perforation of the hear wall is avoided. The set of tines are made such that each tine exhibits the determined characteristics (i.e. cross-sectional area characteristic of a distal end of each tine, and a substantially high confidence level characteristic exists that perforation is avoided).

One or more other embodiments relate to dislodgement of the set of tines (i.e. nitinol tines), which behave in a manner similar to springs. In this embodiment, the lead tip is typically pulled and/or displaced more than about 50% the length of the tine, which is typically above a force threshold in order to cause dislodgement. Force threshold is the minimal amount of force required to dislodge one or more tines from the tissue. In another embodiment, the tine tip is moved 90 degrees from its original position to cause dislodgement. Any force, applied to the lead that does not result in dislodgement, will not affect the pacing threshold since the tines automatically spring back into their original position.

The details of one or more aspects of the disclosure are set forth in the accompanying drawings and the description below. Other features, objects, and advantages of the disclosure will be apparent from the description and drawings, and from the claims.

BRIEF DESCRIPTION OF THE DRAWINGS

FIG. 11A depicts a schematic view of the initial implant stage in which the delivery system including the lead is positioned near the right atrial appendage (RAA) while the tines are retracted to avoid snagging the tines on any anatomical areas.

FIG. 11B depicts a schematic view of the delivery system is placed or pushed in the appendage in the desired target location.

FIG. 11C depicts a schematic view of the delivery system during the process of deploying the tines.

FIG. 11D depicts a schematic view of the delivery system moving in a proximal position thereby causing tines to contact the epicardial surface.

FIG. 11E depicts a schematic view of lead tines that are deployed.

DETAILED DESCRIPTION OF EXEMPLARY EMBODIMENTS

Figure 1:
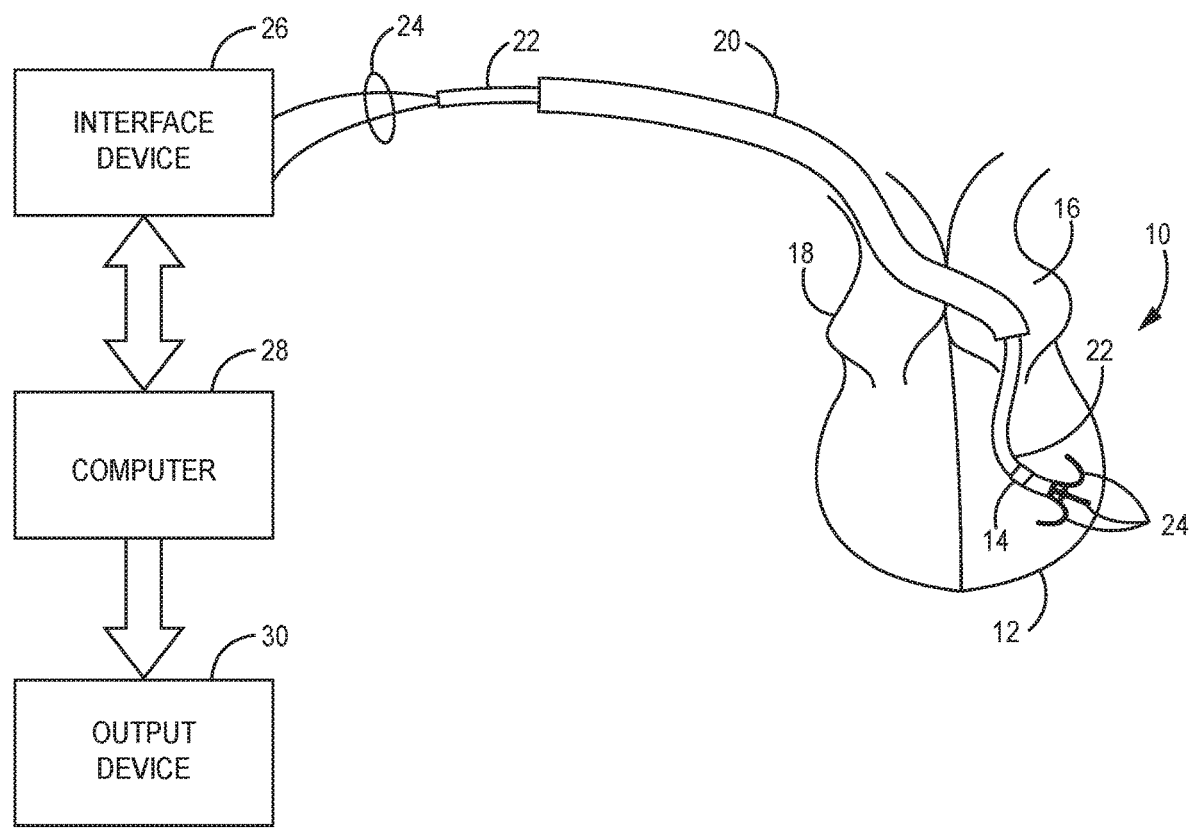
FIG. 1 is a diagram illustrating a lead in the process of implantation and an associated device system for obtaining the parameters to be measured and for providing an indication of the fixation of tines that have entered heart tissue.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary systems, methods, and interfaces shall be described with reference to FIGS. 1-13. It will be apparent to one skilled in the art that elements or processes from one embodiment may be used in combination with elements or processes of the other embodiments, and that the possible embodiments of such methods, apparatus, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

FIG. 1 illustrates a patient's heart 10, with a lead 22, introduced into the left ventricle 12 by means of an introducer catheter 20. The lead is subsequently connected to an implantable medical device (IMD). IMD refers to a pacemaker, an implantable cardioverter-defribrillator (ICD), a leadless pacemaker device (e.g. Micra®) or other implantable therapy delivery assembly configured to deliver electrical stimulation. The lead 22 is introduced into or onto the left ventricle by means of an atrial trans-septal puncture allowing the introducer catheter to enter the left atrium 16. The lead 22 is then moved onto the left ventricle 12. A ventricular trans-septal puncture may also be employed. Tines 24 are shown extending from the distal end of lead 22 and adjacent the wall of the left ventricle 12. A single tine is a NiTi tension cantilever spring.

Exemplary tines 24 are shown and described in an article published by the inventors of the present disclosure, the citation of which is Michael D. Eggen et al., i Design and Evaluation of A Novel Fixation Mechanism for a Transcatheter Pacemaker, IEEE TRANSACTIONS ON BIOMEDICAL ENGINEERING, vol. 62, No. 9, (Sep. 9, 2015), the entire disclosure is incorporated herein by reference in its entirety.

In other embodiments, the lead 22 may be placed in other locations, including the atria (i.e. right, left) and/or the right ventricle. The specific relationships between the measured parameters and the tines may vary with lead configuration and location. Correspondingly, the measured parameters indicative of proper fixation may also vary.

The lead 22 is coupled by lead conductors—to an interface device 26 such as a Medtronic Model 2290 Pacing Systems Analyzer (PSA). The interface device 26 is used to make the measurements of the parameters and provides the measurements to the computer 28. In some embodiments, the collection of the measured parameters may be done under physician control when determining a location to implant a lead 22. In other embodiments, collection of the parameters may be done under control of computer 28 or under control of software resident in the interface device 26. The computer 28 employs the analytical methodology of the present invention to derive measurements and provide it to the output device, which may be a conventional display. The analytical techniques of the present invention, as discussed below, may be embodied in stored software as executed by computer 28.

Figure 2:
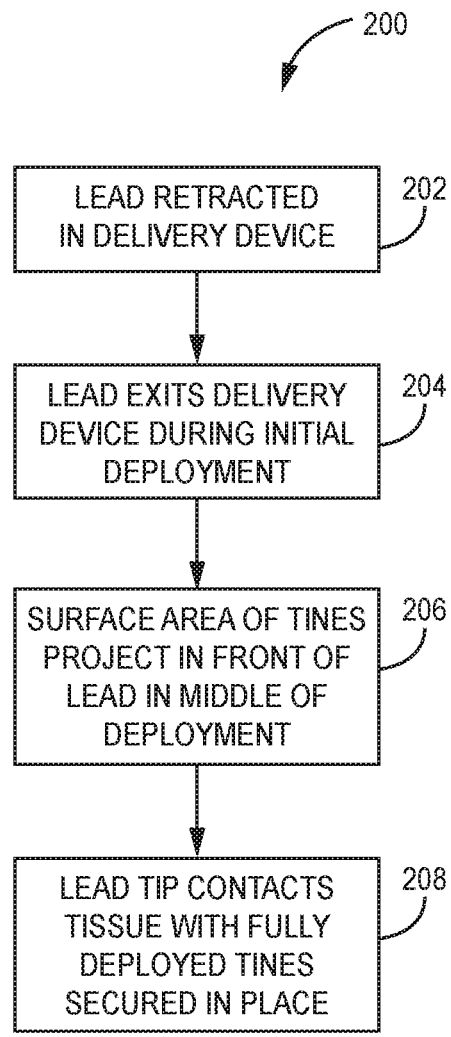
FIG. 2 is a flow chart illustrating a first embodiment of the analytical method performed by the device system of FIG. 1.
Figure 3A:
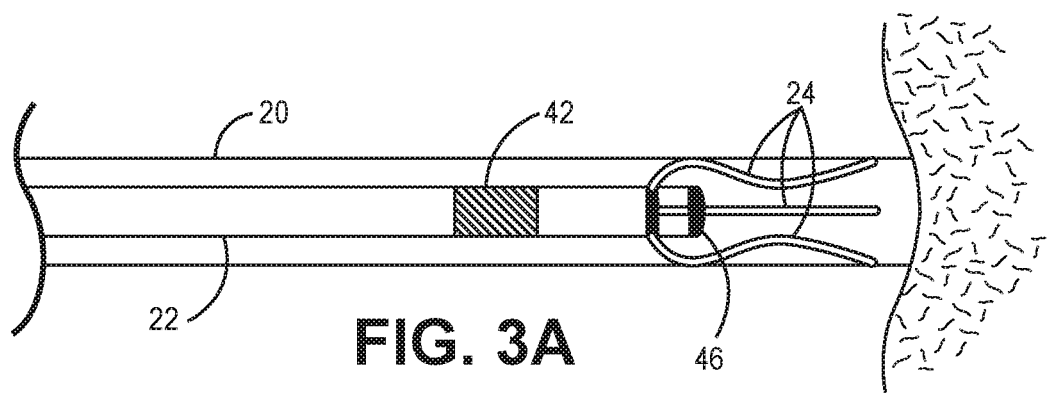
FIG. 3A is a schematic diagram depicting pre-deployment of the set of tines occurring such that the lead and tines are retracted in the delivery catheter and the delivery catheter is placed against the myocardium.
Figure 3B:
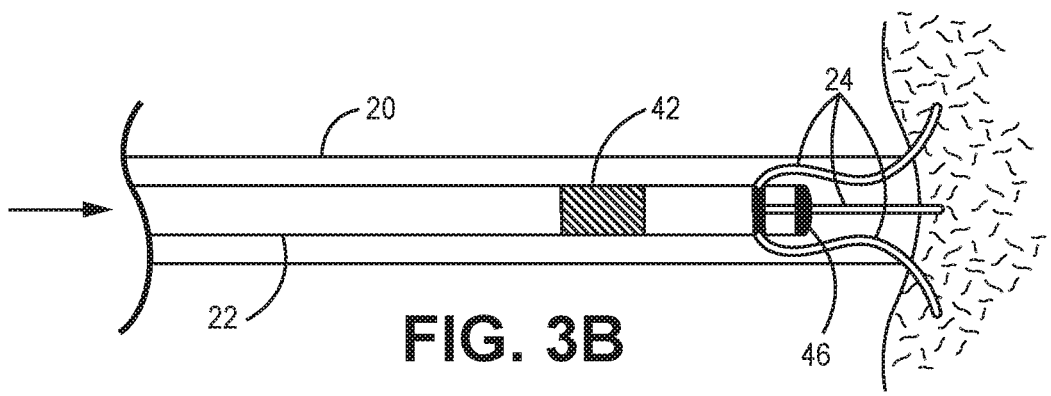
FIG. 3B is a schematic diagram depicting during the initial stage of the deployment, the tines are immediately positioned at an angle as soon as tines exit the catheter and start penetrating tissue.
Figure 3C:
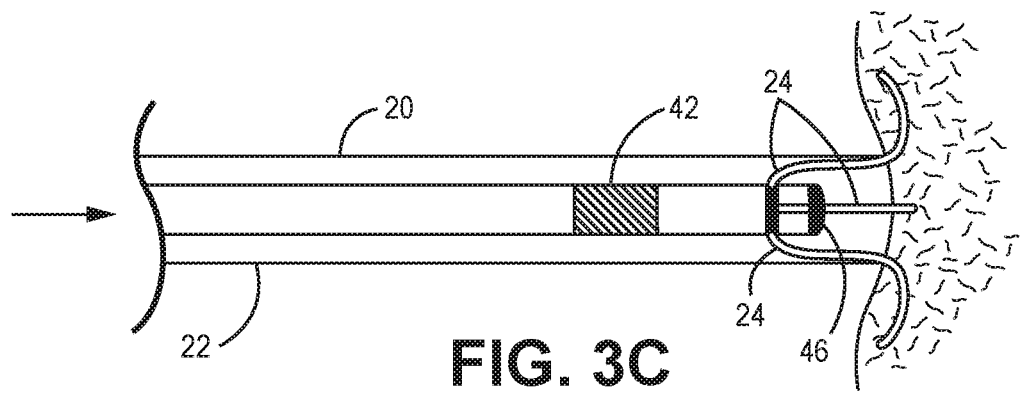
FIG. 3C is a schematic diagram that shows during the middle of the deployment sequence, the majority of the surface area of tines is projected in front of the lead, even before the lead body touches tissue.
Figure 3D:
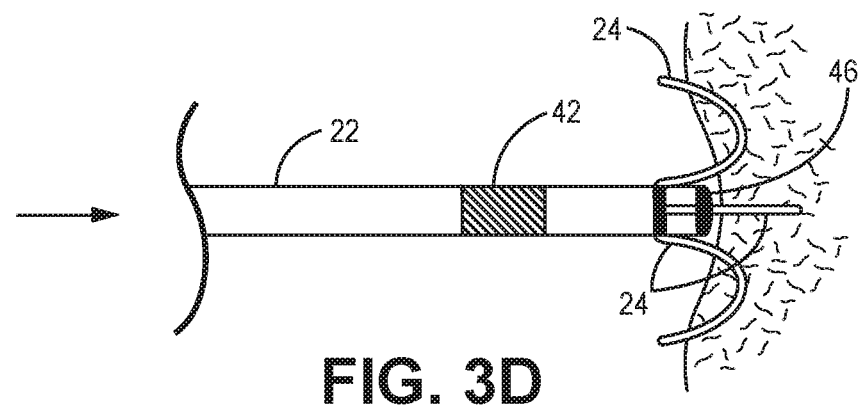
FIG. 3D is a schematic diagram that shows after full deployment of the lead such that the lead tip is touching or in contact with tissue, and the surface area of the fully deployed tines prevents any acute or chronic migration of the lead body.

FIG. 2 is a flow chart illustrating operation of a first embodiment deployment technique according to the present disclosure. At blocks 200, 202, 204, 206, the computer 28 (FIG. 1) receives the input measured parameters from the interface device 26. Method 200, shown relative to FIGS. 3A-3D, depicts sequential steps of tine deployment and tissue attachment relative to FIG. 2. In particular, method 200 discloses the steps of the deployment sequence as to how the tines come out first and increase the frontal area during deployment, in order to reduce lead body perforation. At block 202 (FIG. 3A), pre-deployment occurs such that the lead 22 and tines 24 are retracted in the delivery catheter 20 and the delivery catheter 20 is placed against the myocardium. An exemplary delivery catheter may be the Attain® Deflectable Catheter Delivery System (Model number 6227DEF) commercially available from Medtronic, Inc., the manual of which is incorporated herein by reference in its entirety. The catheter kit comes with a dilator, which is an inner catheter to transition from a guidewire to the catheter. The inner diameter of the deflectable catheter is 7.2 French (2.4 mm). The inner diameter of the dilator is 7 French (2.3 mm). The length of the dilator is 60 cm. Any catheter less than 7.2 French will pass through the deflectable catheter. Skilled artisans appreciate any type of delivery catheter may be employed to deliver a lead to cardiac tissue.

At block 204 (FIG. 3B), during the initial stage of the deployment, the tines 24 are immediately positioned at an angle as soon as tines 24 exit the catheter 20 and start penetrating tissue. This angle increases the frontal surface area of the tine 24 resisting lead body motion, while anchoring the tines 24 in the tissue. At block 206 (FIG. 3C), during the middle of the deployment sequence, the majority of the surface area of tines 24 is projected in front of the lead 22, even before the lead body touches tissue. At block 208 (FIG. 3D), after full deployment of the lead 22, the lead tip is touching or in contact with tissue, and the surface area of the fully deployed tines prevents any acute or chronic migration of the lead body.

In one or more embodiments, the set of times are solely configured to penetrate viable cardiac tissue and cannot penetrate poor substrates (e.g. scar tissue), arteries, or veins. If the location is suitable for cardiac pacing and sensing, based upon measured response from cardiac tissue, the physician may leave the lead 22 in place. In one or more embodiments, the physician may re-position the lead 22 at another location, and the analytical process is re-started as described above.

Prior to implant, the tines are straightened by the delivery tool 20 so that the tines point distally with respect to the device. The lead tines are aligned to have their tips contact heart tissue and stores potential energy needed during implant to fixate (i.e., penetrate). Sharp tips on the tine reduces the amount of energy needed to implant the device but it would also reduce the amount of force needed to damage tissue during removal. For this reason, the tine tip and the tine sides, shown in greater detail with respect to FIG. 13, must be curved so that no sharp corner is in contact with the tissue during removal.

Since the tines are curved, an exact cross-sectional area of the tine is difficult to specify. Furthermore, the amount of force needed by the tines to fixate to the tissue will depend on the surface area of the tissue that is in contact with the tine. The amount of surface area of the tissue that is in contact with the tine is based on the surface area of the distal end of the tine.

Safety features of the design are based on the retraction characteristics of the fixation mechanism. Performance features are based on deployment characteristics of the fixation mechanism. By design, safety and performance features are governed by delivery tool work and/or energy input (i.e. offset) that is controlled by operator by tactile feedback. Tactile feedback is the response sensed by the user when moving the delivery system in position and/or placing the lead. Work/energy (Wintg (J)) is the area under the force-displacement curve of the penetration.

At the time of implant, the compound force of the tine spring (FmaxD) and the delivery tool capsule ejection acts on the effective cross-sectional area of the tine over the tine length 38 needed to imbed into the tissue (dD). dD involves deployment displacement of the full cycle test.

The sum of potential energy of the fixation stored in the tine spring and delivery tool capsule ejection mechanism can be important, in one or more embodiments, for balancing the need to fixate reliably and the ability to reposition the device when needed with minimum damage to the tissue. Potential fixation energy of the tine at deployment (WingtgDFmax) is only about 34% of the fixation energy of the tine at retraction (WingtgRFmax). WingtgDFmax (Maximum force at deployment) is the potential fixation energy of the tine at deployment defined by the end of the force plateau (i.e. typically maximum peak force) and the displacement needed to reach the end of the force plateau. WingtgRFmax is the potential fixation energy of the tine at retraction defined by the end of the force plateau (i.e. typically maximum peak force) and the displacement needed to reach the end of the force plateau.

The amount of energy provided by the delivery tool capsule ejection mechanism (or pushing on the lead) can be defined as the offset difference in energy needed to equal fixation potential energy of deployment to the fixation energy of the retraction.

Making deployment potential energy essentially equivalent to the retraction potential energy allows the design to maintain high reliably of fixation within the use conditions defined by the tissue properties while also permitting the design to be safely repositionable. The amount of energy needed to fixate is proportional to the effective cross-sectional area of the penetrator. The penetrator, similar to a tine, is used to during testing with tissue. The amount of energy needed to fixate is primarily determined by the properties of the endocardial layer of the heart wall.

The amount of energy needed to retract the fixation mechanism is significantly impacted by the properties of the epicardial layer of the heart wall. The determination that the epicardial layer affects the amount of energy needed to retract the fixation mechanism was based on a comparison of work/energy needed to tent the tissue under penetration tests. Penetration occurs when an object enters the heart wall but does not go completely through it.

Reviewing tissue penetration data, it was observed that significantly more work and/or energy is needed to dome the tissue from the epicardial surface (i.e. inside/out) than endocardial surface (i.e. outside/in) up to a penetration point with the equivalent penetrator. Inside/out (IO) penetration is penetration moving from the endocardium to the epicardium. Outside/in (OI) penetration is penetration moving from the epicardium to the endocardium.

The effective length of the tine (dR or dD) is optimized by design to be in the range of the low limit point and the high limit point of the I/O and O/I tissue population of the displacement. A low limit point is a point at which there is the largest difference in distribution of inside/out penetration population to outside/in penetration population. A high limit point is 95% of the I/O population for the force and displacement while 100% efficiency point for work.

In-vivo, the delivery tool 20 provides an offset needed to increase the length of the tine that reaches maximum peak force of the deployment (dDFmax) to achieve displacement needed to penetrate endocardial layer. The user or operator of the delivery tool 20 can maintain control of the delivery by tactile feedback.

The length of the tine that reaches maximum peak force of deployment (dDFmax) and length of the tine that reaches maximum peak force of the retraction (dRFmax) is considered equivalent about equivalent. This balances the mechanism at retraction and deployment. dRFmax is defined as the length of the tine that reaches the end of the force plateau (i.e. typically maximum peak force) of the retraction process.

The length balance provides a safety advantage by minimizing the length of the tine in contact with the tissue at retraction. The length of the tine in contact with the tissue at retraction limits the potential energy resisting tissue at the retraction of the fixation mechanism. Observing the distribution of the O/I tissue penetration length needed to reach the maxim peak force of penetration, length of the tine that reaches maximum peak force of the retraction (dRFmax) should be less than 95% of the population.

Figure 4:
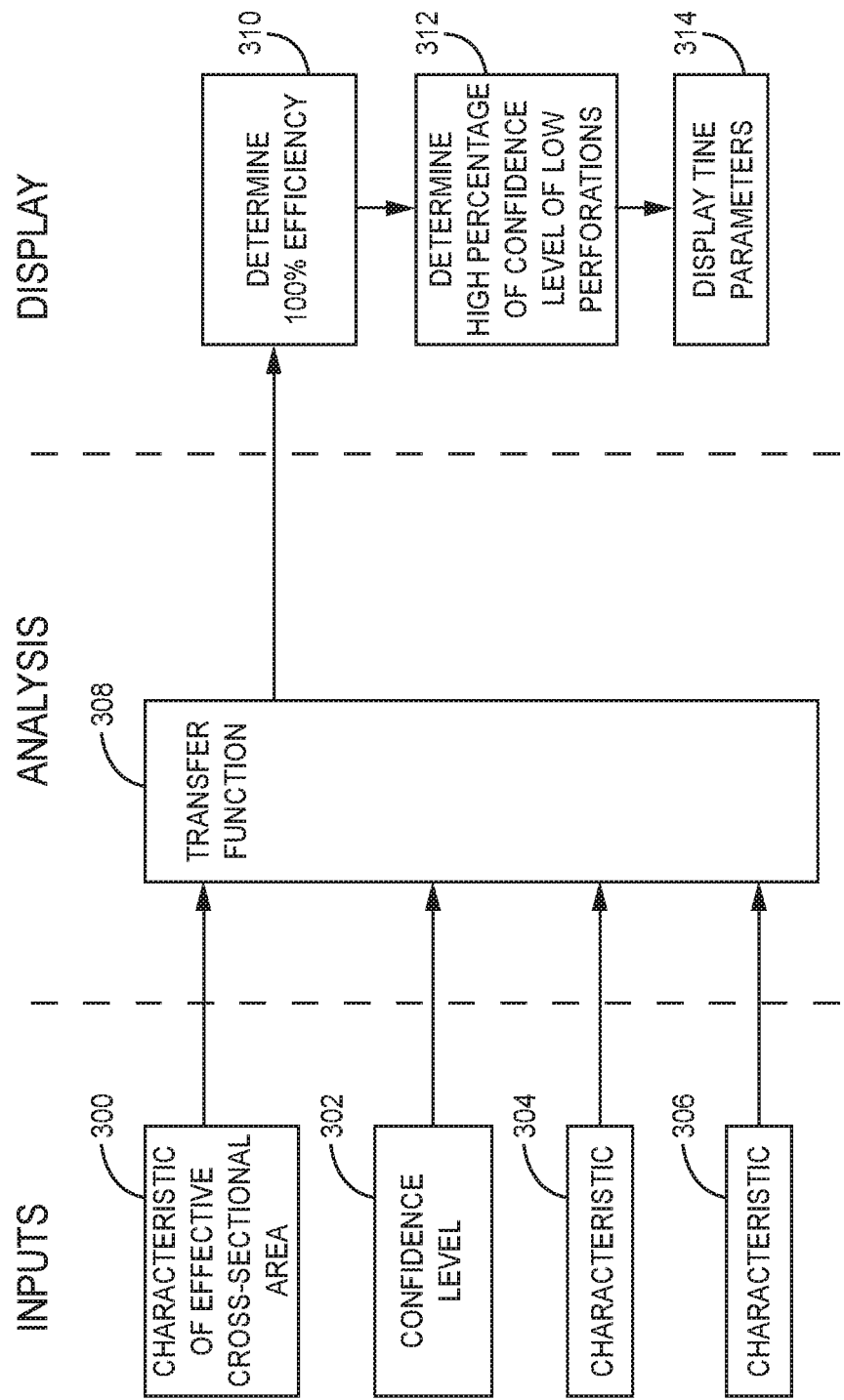
FIG. 4 is a flow chart illustrating a method of determining characteristics of a set of tines employing an analytical method according to the invention.
Figure 5:
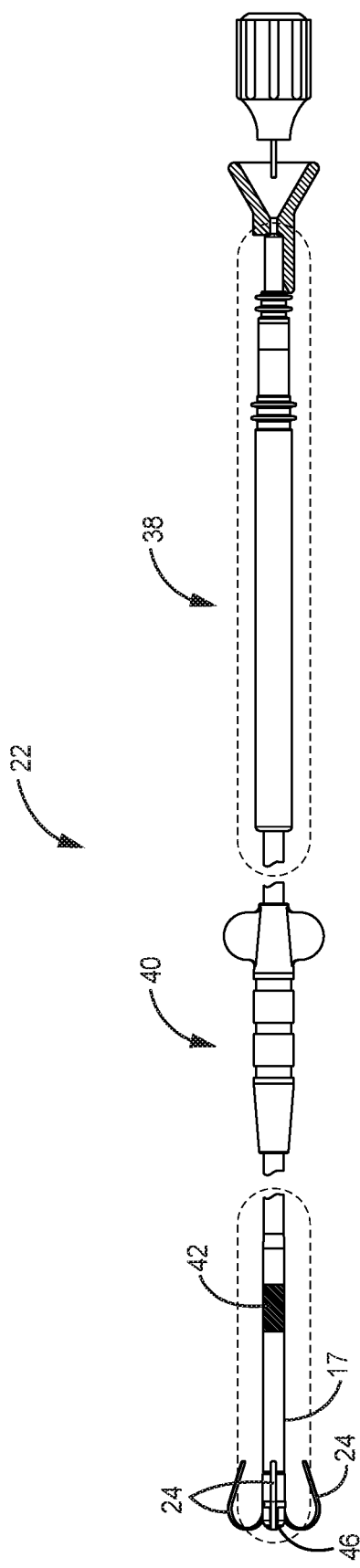
FIG. 5 depicts a schematic view of a medical electrical lead with a set of tines at a distal end of the lead.
Figure 6:
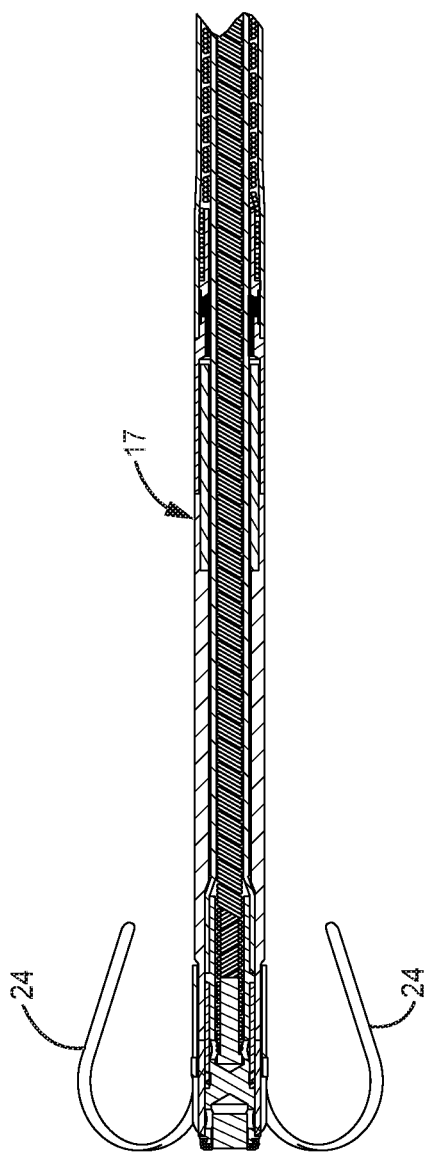
FIG. 6 depicts a schematic and cross-sectional view along a longitudinal axis defined by lines 5-5 of a distal end of medical electrical lead with a set of tines at a distal end of the lead.
Figure 7:
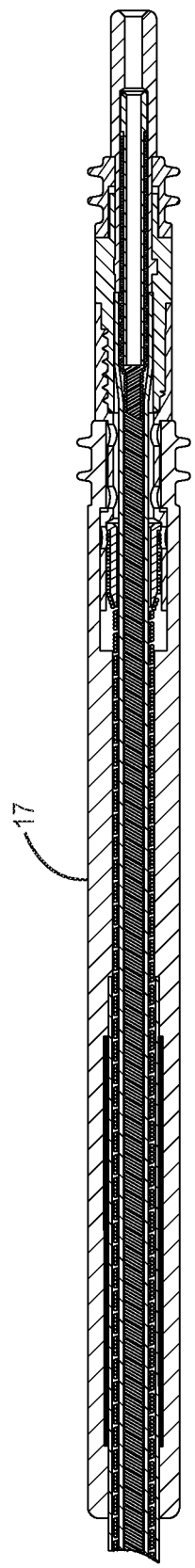
FIG. 7 depicts a schematic and cross-sectional view along a longitudinal axis defined by lines 5-5 of a medical electrical lead body.
Figure 8:
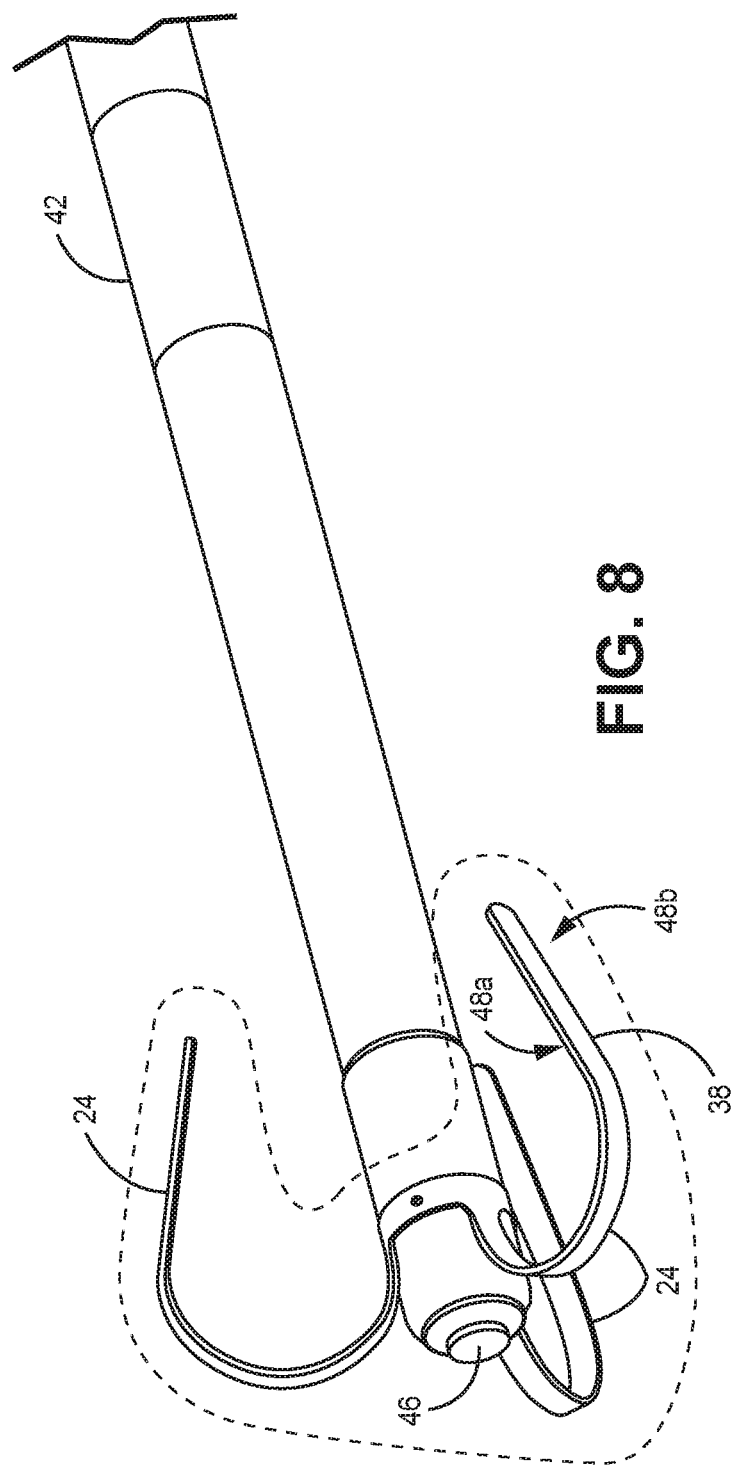
FIG. 8 depicts a schematic view of a medical electrical lead with a set of tines at a distal end of the lead.
Figure 9:
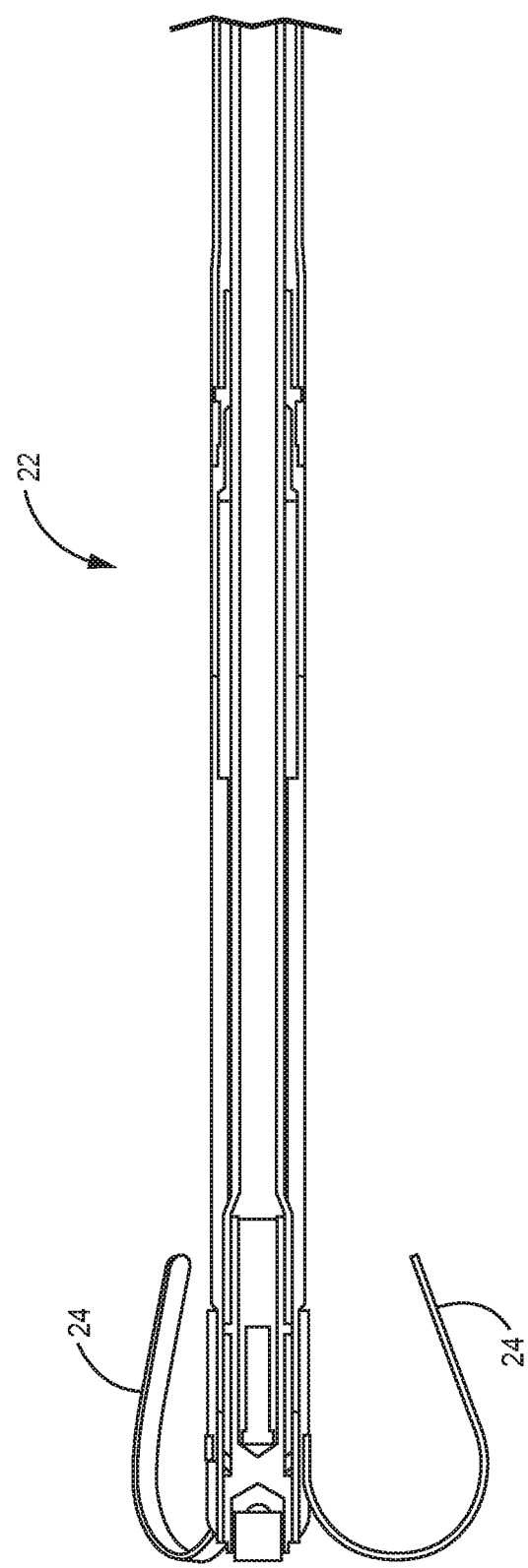
FIG. 9 depicts a schematic and cross-sectional view along a longitudinal axis defined by lines 8-8 of a medical electrical lead with a set of tines at a distal end of the lead.

FIG. 4 is a flow diagram illustrating a method of determining characteristics of a set of tines employing an analytical method according to the invention. A computer with a graphical user interface or display is used to determine the characteristics of the tines. Inputs 300, 302, 304, 306, are received by the processor of the computer for analysis. Block 300 is the effective cross-sectional area of the tine, which is calculated using the first transfer function, provided below. The confidence level input is provided as input 302. The confidence level input is defined by the user. A high confidence level is selected that perforations will not occur. For example, a user may select a 95% confidence level that no perforations occur. A high and low limit is selected in which that assess damage to the tissue. Other exemplary inputs 304, 306 for design parameters (also referred to as tine characteristics) include width of the tine, thickness of the tine, radius of a curve for the tine, length of the straight section. Additional or alternative embodiments for design parameters include fixation mechanism material properties, implant medium material properties (i.e. tissue properties), desired confidence level, desired reliability level, use conditions, fatigue performance, etc.

In one preferred embodiment, a 95% or more (e.g. 100%) efficiency is displayed to the user at block 310 which indicates that the set of tines do not dislodge while a high confidence level at block 312 is selected that perforations will not occur. Additionally or alternatively, other data can be displayed to the user such as performance level (i.e. holding force-displacement-energy), projection of reliability bounds over time. Blocks 310, and 312 are not calculated using the first transfer function. Rather, these are limits that assist in determining the tines characteristics which are displayed at block 314.

Figure 10:
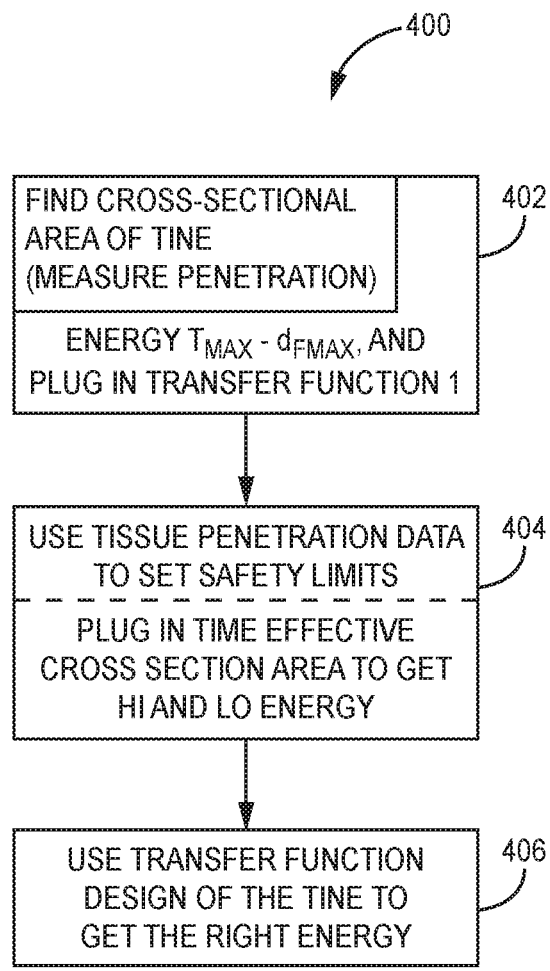
FIG. 10 is a flow diagram depicting a method of making a lead with tines.

FIG. 10 is a flow chart depicting how to form tines for a lead 22. At block 402, the cross-sectional area of the distal end of the tine is selected. Once the cross-sectional area of the distal end of the tine has been selected, the effective cross-sectional area of the tine is determined by using the first transfer function. The exemplary first transfer function is as follows:

$Wintg(J)$(Chamberlain Group Part Number 1361)
  =$0.0063 \times Agp\_ecs(mm^2) - 0.0004$   Transfer Function 1

Effective cross-sectional area ($Agp\_ecs$ ($mm^2$)) is the area of the penetrator tip in contact with the tissue referenced to a standard (i.e. the flat bottom cylinder gauge pin). The tissue, in which the tines 24 will be attached thereto, is tested to determine the high and low level amount of energy that will potentially cause damage to the tissue. For example, assume the right ventricular tissue is to be tested the energy and the displacement associated with the energy are calculated through the first transfer function. The effective cross-sectional area for the distal end of the tine is plugged into the high and low level transfer functions.

The high and low level limits that assess damage to the tissue are provided by the following transfer functions:

$Wintg(J) = 1.339E\text{-}02 \times Agp\_ecs(mm2) - 6.984E\text{-}04 R^2 = 0.963$ High level limit transfer function
The low level limit is provided by the following transfer function:
  Regression equation for the biggest percent-difference IO to OI of the displacement d (mm):

$Wintg(J) = 1.339E\text{-}02 \times Agp\_ecs(mm2) - 6.984E\text{-}04 R^2 = 0.963$ Displacement (d (mm)) refers to the depth of material tented under the load applied by the penetrator of known effective cross-sectional area. The distance the penetrator has traveled to displace tissue before entering the tissue.

FIGS. 11A-11E show a process for deploying the set of tines in the right atrial appendage (RAA). FIG. 11A depicts a schematic view of the initial implant stage in which the delivery system 20, including the lead, is positioned near the RAA while the tines are retracted to avoid snagging the tines on any anatomical areas. The distal end of the delivery system 20 directly faces the pectinate muscle and has not contacted the epicardial layer of the heart. While moving the delivery system 20, the physician employs an imaging system such as fluoroscopy in order to position the delivery system in pectinate structure.

FIG. 11B depicts the delivery system being placed or pushed in the appendage to the desired target location. Once the physician begins pushing on the lead 20, the effective length of the tine inside the heart is changing because the lead is exiting delivery system 20. Delivery system 20 configured to be soft or flexible and is opposing the reaction force of the tines. Thus, the delivery system 20 is applying a limiting force that can be applied to the tissue by the delivery system 20 thereby deflecting back. The delivery system in combination with the lead designed with tines is an improvement over conventional delivery systems. For example, one type of conventional delivery system 20 is extremely rigid and the lead is also very rigid. The combination of the conventional delivery system and the lead would not move. Consequently, the resulting pressure from the stiff delivery system and lead would force the tines through the heart wall in contrast to the delivery system 20 of the present disclosure.

FIG. 11C depicts a schematic view of the delivery system during the process of deploying the tines. The tines penetrate the pectinate muscle and reached the tougher endocardial layer. The delivery system energy balance with tissue energy when only the pectinate muscle is penetrated by the tines. The tines can pierce the pectinate muscle and contact the epicaridal surface. The tines can move along side the epicardial surface.

FIG. 11D depicts a schematic view of the delivery system in which a "kick back" force causes the delivery system to move in a backward motion from its position. In response to the "kick back", the tines contact the epicardial surface.

FIG. 11E depicts a schematic view of the delivery system such that when the tines contact the epicardial surface, the delivery system (i.e. catheter) column strength was not sufficiently stiff to allow tines to penetrate tougher layers. The delivery system "kicks back" and thereby limits the tip force. The tines are then completely deployed.

Figure 12A:
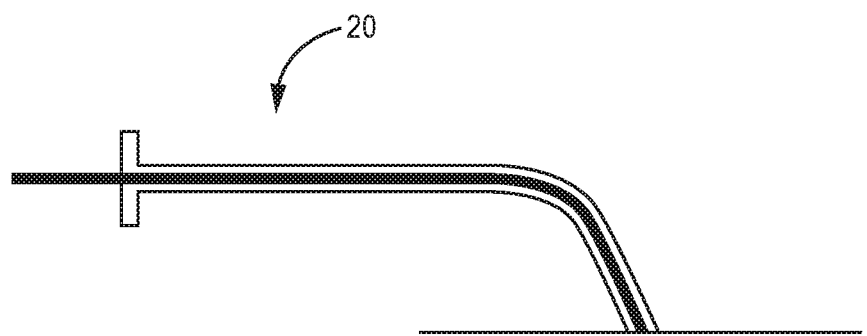
FIG. 12A depicts a schematic view of the delivery system in which the delivery system is flexible as shown by a bend and angle in the delivery system.
Figure 12B:
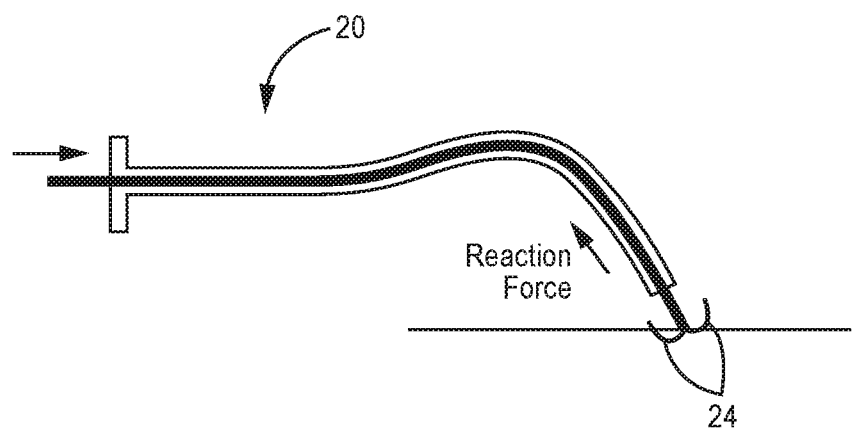
FIG. 12B depicts a lead attached to tissue.

FIGS. 12A-12B depict a delivery system (or delivery catheter) that can only provide enough reaction force to penetrate the pectinate layer of the RAA. As shown, the tines are angled toward the target tissue (e.g. RAA) which is achieved by the delivery system bending and pivoting due to the flexibility in the delivery system (i.e. catheter). FIG. 12A depicts a delivery system 20 in which the distal end of the delivery system is angled toward the target tissue site. FIG. 12B depicts a delivery system 20 in which the tines on the lead are attached to the tissue at an angle while the delivery system is bending and pivoting.

Figure 13A:
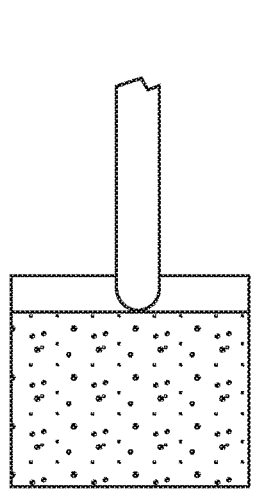
FIG. 13A depicts a straight section of the tine-tissue interface during initial penetration of the endocardial surface
Figure 13B:
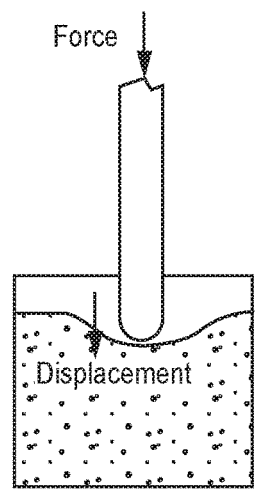
FIG. 13B depicts a straight section of the tine-tissue interface after initial penetration of the endocardial surface.
Figure 13C:
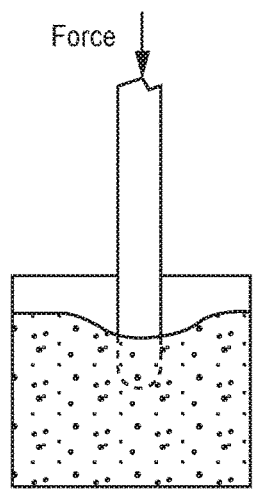
FIG. 13C depicts a straight section of the tine-tissue interface in which greater force is applied to the tine.
Figure 13D:
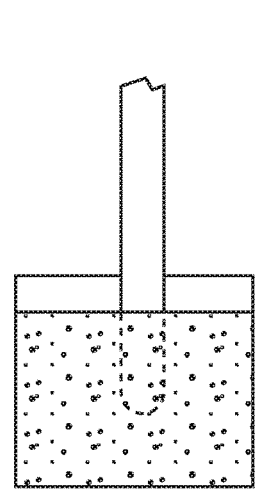
FIG. 13D depicts a straight section of the tine-tissue interface in which the tine has fully penetrated the tissue.

FIGS. 13A-13-D illustrate of the straight section of the tine-tissue interface during initial penetration of the endocardial surface. A force is applied to the tine tip, which displaces the tissue (i.e. tenting) and generates pressure (FIG. 13A and FIG. 13B). As the tine moves forward and the tissue continues to displace, the pressure increases to the point at which the tine penetrates the tissue (FIG. 13C). Once the tissue is penetrated, the pressure is relieved and the tissue returns to its native position (FIG. 13D).

Lead 22 can be implanted in many different locations in the heart. For example, lead 22 can be placed inside the right atrium or right ventricle. The acute perforation properties of the right atrial appendage (RAA) were determined to provide superior results with respect to fixation to the tissue while exhibiting limited perforations of the thinly-walled right atrium.

Estimated rates of acute pacemaker lead perforations range between 0.5-2%, establishing significant clinical and device design considerations. Although pericardial effusion may result from perforation and can be a significant clinical issue, limited research has investigated the biomechanical properties of atrial tissue. A study was performed to better define the relationship between perforation forces of the right atrial appendage (RAA) and the surface areas of the applied penetrating devices (e.g. a lead or fixation mechanism).

For this study, to date, the RAA was dissected from swine (n=10) and human (n=1) donor hearts and secured in a custom chamber. An oxygenated Krebs-Henseleit buffer promoted tissue viability, and maintained tissue temperature at 37° C. Cylindrical penetrators diameters between diameter=0.25-12.7 mm were quasi-statically advanced at 120 mm/min until perforation occurred. Quasi-static means that the motion during the perforation is so slow that no dynamic effects occur.

Perforation forces of pectinate muscle and the epicardium of the RAA were investigated (swine, n=280 penetrations; human, n=40 penetrations).

The perforation forces ($F_P$: Newtons) vary linearly with penetrator cross-sectional area (CSA: $mm^2$) for both pectinate muscle (swine, $F_P=0.97*CSA+0.28$, $R^2=0.54$; human, $F_P=3.14*CSA+0.23$, $R^2=0.16$) and epicardium of the RAA (swine, $F_P=1.62*CSA-0.63$, $R^2=0.58$; human, $F_P=6.62*CSA+0.61$, $R^2=0.22$). $F_p$ for epicardial tissue was significantly higher than $F_p$ for pectinate muscle for all penetrators ($p<0.05$). Perforations of lateral wall pectinate required greater forces than perforations of the distal tips of the RAA (95% CI for slope [1.01, 1.34] vs [0.63, 0.82]). Perforations of the epicardial layer within various anatomical RAA locations required no significant difference in force.

The present disclosure provides one or more approaches to assess perforation properties within the RAA of both human and swine hearts. We studied both pectinated and thin walled regions in multiple anatomical locations within the RAA. This biomechanical information can optimize the design and implementation of novel atrial fixation technologies.

The set of tines can be secured to a variety of medical electrical leads. FIGS. 5-8 depict a schematic view of a medical electrical lead 22 with a set of tines at a distal end of the lead 22. Lead 22 can be configured from a variety of lead bodies. Exemplary leads fitted with the crown (shown in ghost lines in FIG. 8) in which set of tines extending therefrom can be the CAPSURE SENSE® 4074 commercially available from Medtronic, Inc., the ISLOFLEX™ commercially available from St Jude Medical, and the INGEVITY™ MRI lead commercially available from Boston Scientific. The manuals for the CAPSURE SENSE® 4074, ISLOFLEX™ and the INGEVITY™ MRI lead are incorporated by reference in their entirety. Skilled artisans understand that set of tines can be configured to be secured to any lead as long as the design requirements set forth herein are met.

Lead 22 includes an elongated lead body 17 that extends from a proximal end to a distal end. The lead body 17 can include one or more jacketed elongated conductive elements. A jacket (also referred to as a layer, longitudinal element, coating) extends along and longitudinally around the conductive elements and serves to insulate one or more conductive elements.

Electrically conductive elements for lead 22 can include coils, wires, coil wound around a filament, cables, conductors or other suitable members. Conductive elements can comprise platinum, platinum alloys, titanium, titanium alloys, tantalum, tantalum alloys, cobalt alloys (e.g. MP35N, a nickel-cobalt alloy etc.), copper alloys, silver alloys, gold, silver, stainless steel, magnesium-nickel alloys, palladium, palladium alloys or other suitable materials. Electrically conductive element is covered, or substantially covered, longitudinally with a jacket (also referred to as a layer, a longitudinal element, a longitudinal member, a coating, a tubular element, a tube or a cylindrical element). Typically, the outer surface of electrodes such as the ring electrode, the tip electrode, and the defibrillation coils are exposed or not covered by a jacket or layer so that electrodes can sense and/or deliver electrical stimuli to tissue of a patient.

Active fixation mechanisms such as the tines, are located at the distal end 44 of lead 22. Optionally, one or more of the electrodes, can be drug eluting such as that which is disclosed in US 20140005762 filed Jun. 29, 2012, assigned to the assignee of the present invention, is incorporated by reference in its entirety. As shown, the electrode 42 (i.e. serving as an anode) is located proximal to the tines 24 and the tip electrode 46 (i.e. serving as a cathode). Additionally, the tip and ring electrodes can be coated with titanium nitride (TiN).

Exemplary liners for lead 22 that can be used in conjunction with the present disclosure are shown and described with respect to U.S. Pat. No. 8,005,549 issued Aug. 23, 2011, U.S. Pat. No. 7,783,365 issued Aug. 24, 2010, and assigned to the assignee of the present invention, the disclosure of which are incorporated by reference in their entirety herein. ATTAIN PERFORMA™ Model 4298 quadripolar lead insulation is another exemplary insulative material that can be used Examples of connector modules may be seen with respect to U.S. Pat. No. 7,601,033 issued Oct. 13, 2009, U.S. Pat. No. 7,654,843 issued Feb. 2, 2010, and assigned to the assignee of the present invention, the disclosure of which are incorporated by reference in their entirety herein. The connector module can take the form of an IS-4 bipolar connector, but any appropriate connector mechanism may be substituted. Connector module 14 electrically couples a proximal end of each lead to various internal electrical components of implantable medical device 10 through a connector or set screw.

Performance of the tines achieved the prespecified conditions set forth herein. The tines were evaluated relative to attachment to tissue or tissue-like conditions. The intersection of the tissue conditions performance region and the performance population distributions defines a successful fit of the prototypes of the tines. Specifically, effective cross-sectional area characteristic of the distal end of each tine fell between a high limit point regression line and low limit point regression line. The tines satisfied tissue use conditions when the resultant data fell within the high limit and low limit lines intersected.

It should also be noted that leads may also be employed for stimulation of other tissue types besides cardiac tissue. The present invention is believed to be adaptable to such uses as well. In such cases, thresholds for stimulation for the tissue type and amplitudes of signals sensed from the tissue would be substituted for pacing threshold and R-wave amplitude as is appropriate. Additionally, other measured parameters of the other tissue types may be substituted for those discussed above or may be used in addition to those discussed above.

The present disclosure includes the following embodiments:

Embodiment 1 is a system for implantation of a lead medical electrical lead in contact with heart tissue, comprising:
    an elongated lead body;
    a set of curved tines mounted to and extending from a distal end of the lead body, the tines having a length (dD) and an effective cross sectional area;
    a delivery catheter, enclosing the lead body and having a distal capsule portion enclosing the tines, the tines exerting a spring force against the capsule and providing a stored potential energy, the delivery catheter having an ejection means for advancing the lead and tines distally from the capsule and fixating the tines within the heart tissue, the ejection means and the stored potential energy of the tines together providing a deployment energy, the tines when so fixated in the tissue providing a fixation energy; and wherein the deployment energy and the fixation energy are equivalent.

Embodiment 2 is system as in embodiment 1, wherein the deployment energy provides a provides a maximum peak force of deployment (dDFmax) and the fixation energy provides a maximum peak force of the retraction (dRFmax) and wherein the length of the tines (dD) is such that (dDFmax) and (dRFmax) are equivalent.

Embodiment 3 is the system according to any of embodiments 1 or 2, wherein (dRFmax) falls between a level sufficient to penetrate the heart tissue from an epicardial surface thereof (O/I) and a level sufficient to penetrate the heart tissue from an endocardial surface thereof (O/I).

Embodiment 4 is a system according to any of embodiments 1-3 wherein the potential energy provided by the spring force of the tines against the capsule is less than the fixation energy.

Embodiment 5 is a system for implantation of a lead medical device in contact with heart tissue, comprising:
    a medical device;
    a set of curved tines mounted to and extending from a distal end of the device, the tines having a length (dD) and an effective cross sectional area;
    a delivery catheter, enclosing the device and having a distal capsule portion enclosing the tines, the tines exerting a spring force against the capsule and providing a stored potential energy, the delivery catheter having an ejection means for advancing the tines distally from the capsule and fixating the tines within the heart tissue, the ejection means and the stored potential energy of the tines together providing a deployment energy, the tines when so fixated in the tissue providing a fixation energy; and
    wherein the deployment energy and the fixation energy are equivalent.

Embodiment 6 is a system as in embodiment 5, wherein the deployment energy provides a provides a maximum peak force of deployment (dDFmax) and the fixation energy provides a maximum peak force of the retraction (dRFmax) and wherein the length of the tines (dD) is such that (dDFmax) and (dRFmax) are equivalent.

Embodiment 7 is a system according to any of embodiments 5 or 6, wherein (dRFmax) falls between a level sufficient to penetrate the heart tissue from an epicardial surface thereof (O/I) and a level sufficient to penetrate the heart tissue from an endocardial surface thereof (O/I).

Embodiment 8 is a system according to any of embodiments 5-7 wherein the potential energy provided by the spring force of the tines against the capsule is less than the fixation energy.

Embodiment 9 is a system according to any of embodiments 5-8 wherein the device is a medical electrical lead comprising an elongated lead body and wherein the tines are mounted to a distal end of the lead body.

Embodiment 10 is a method of making a medical electrical lead type having a set of tines, the method comprising:
    determining effective cross-sectional area characteristic of a distal end of each tine in the set of tines relative to a displacement energy required to displace a set of tissue layers;
    in response to determining the effective cross-sectional area characteristic of the distal end of each tine, determining whether a substantially high confidence level characteristic exists that perforation is avoided; and
    making the set of tines in which each tine exhibits the determined characteristics.

Embodiment 11 is a method according to embodiment 10 wherein a transfer function associates effective cross-sectional area of a distal end of each tine in the set of tines to the displacement energy.

Embodiment 12 is a method according to embodiment 11 wherein the high confidence level is determined based upon 100% efficiency of the set of tines staying in position without dislodging.

Embodiment 13 is a method according to any of embodiments 11-12 comprising configuring the set of times to solely penetrate viable tissue in response to determining the transfer function.

Embodiment 14 is a method according to any of embodiments 10-13 wherein the set of tines are configured to not penetrate veins.

Embodiment 15 is a method according to any of embodiments 10-14 wherein the set of tines are configured to not penetrate arteries.

Embodiment 16 is a method according to any of embodiment 10-15 wherein the set of tines are configured to not penetrate non-viable cardiac tissue.

Embodiment 17 is a method according to any of embodiments 10-16 wherein a transfer function associates effective cross-sectional area of a distal end of each tine in the set of tines to the work/energy.

Embodiment 18 is a method according to embodiment 17 wherein the determining step comprises application of the transfer function derived from testing of leads of the type.

Embodiment 19 is a method according to any of embodiments 17-18 wherein the displacement energy is defined by a peak maximum force and associated displacement.

Embodiment 20 is a method according to any of embodiments 10-19 wherein the tissue is heart tissue.

Embodiment 21 is a method according to any of embodiments 10-20 wherein the tines are configured to provide 100% efficiency of fixation for 95% of a population in which the lead may be implanted.

Embodiment 22 is a method according to any of embodiments 10-21 further comprising selecting a high level point and a low level point to achieve a 100% efficiency of fixation for the 95% of the population.

Embodiment 23 is a method according to any of embodiments 10-22 wherein the tines are configured to provide at least 95% efficiency of fixation for 95% of a population in which the lead may be implanted.

Embodiment 24 is a method according to any of embodiments 10-23 further comprising selecting a high level point and a low level point to achieve at least 95% efficiency of fixation for the 95% of the population.

Embodiment 25 is a method according to any of embodiments 10-24 wherein the set of tines comprises three or more tines.

Embodiment 26 is a system for implantation of a lead medical electrical lead in contact with heart tissue, comprising:
  an elongated lead body;
  a set of curved tines mounted to and extending from a distal end of the lead body, the tines having a length (dD) and an effective cross sectional area;
  a delivery catheter, enclosing the lead body and having a distal capsule portion enclosing the tines, the tines exerting a spring force against the capsule and providing a stored potential energy, the delivery catheter having an pushing means for advancing the lead and tines distally from the capsule and fixating the tines within the heart tissue, the pushing means and the stored potential energy of the tines together providing a deployment energy, the tines when so fixated in the tissue providing a fixation energy; and
  wherein the deployment energy and the fixation energy are equivalent.

Embodiment 27 is a system of embodiment 26 wherein the pushing means is one of a stylet, a guidewire and a hybrid stylet/guidewire.

Embodiment 28 contemplates that the delivery system and medical electrical lead should provide 0.5 Newtons-0.3*(0.5 Newtons) of force and/or energy.

The complete disclosures of the patents, patent documents, and publications cited herein are incorporated by reference in their entirety as if each were individually incorporated. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

The invention claimed is:

1. A system for implantation of a medical device in contact with heart tissue, comprising:
  a medical device;
  a set of curved tines mounted to and extending from a distal end of the device, the tines having a length (dD) and an effective cross-sectional area;
  a delivery catheter, enclosing the device and having a distal capsule portion enclosing the tines, the tines exerting a spring force against the capsule and providing a stored potential energy, the delivery catheter having an ejection means for advancing the tines distally from the capsule and fixating the tines within the heart tissue, the ejection means and the stored potential energy of the tines together providing a deployment energy, the tines when so fixated in the tissue providing a fixation energy; and
  wherein the deployment energy and the fixation energy are equivalent; and
  wherein the deployment energy provides a maximum peak force of deployment (dDFmax) and the fixation energy provides a maximum peak force of the retraction (dRFmax) and wherein the length of the tines (dD) is such that (dDFmax) and (dRFmax) are equivalent.

2. A system according to claim 1, wherein (dRFmax) falls between a level sufficient to penetrate the heart tissue from an epicardial surface thereof (O/I) and a level sufficient to penetrate the heart tissue from an endocardial surface thereof (O/I).

3. A system according to claim 1 wherein the device is a medical electrical lead comprising an elongated lead body and wherein the tines are mounted to a distal end of the lead body.

4. A system according to claim 1 wherein the ejection means comprises a pushing means for advancing the lead and tines distally from the capsule.

5. A system according to claim 4 wherein the pushing means is one of a stylet, a guidewire and a hybrid stylet/guidewire.

6. A system according to claim 1 wherein the deployment energy and the fixation energy are equal.

7. A system according to claim 1 wherein the set of tines comprises three or more tines.

8. A system according to claim 1 wherein the set of tines are configured to solely penetrate viable tissue.

9. A system according to claim 1 wherein the set of tines are configured to not penetrate veins.

10. A system according to claim 1 wherein the set of tines are configured to not penetrate arteries.

11. A system according to claim 1 wherein the set of tines are made of nitinol.

12. A system according to claim 1 wherein the delivery catheter is a deflectable catheter.

13. A system according to claim 1 wherein the tines, when enclosed by the delivery catheter, are straightened to point distally with respect to the medical device.

14. A system for implantation of a medical device in contact with heart tissue, comprising:
- a medical device;
- a set of curved tines mounted to and extending from a distal end of the device, the tines having a length (dD) and an effective cross-sectional area;
- a delivery catheter, enclosing the device and having a distal capsule portion enclosing the tines, the tines exerting a spring force against the capsule and providing a stored potential energy, the delivery catheter having an ejection means for advancing the tines distally from the capsule and fixating the tines within the heart tissue, the ejection means and the stored potential energy of the tines together providing a deployment energy, the tines when so fixated in the tissue providing a fixation energy; and
- wherein the deployment energy and the fixation energy are equivalent; and
- wherein the potential energy provided by the spring force of the tines against the capsule is less than the fixation energy.

15. A system according to claim 14 wherein the device is a medical electrical lead comprising an elongated lead body and wherein the tines are mounted to a distal end of the lead body.

16. A system according to claim 14 wherein the ejection means comprises a pushing means for advancing the lead and tines distally from the capsule.

17. A system according to claim 14 wherein the set of tines are configured to solely penetrate viable tissue.

18. A system according to claim 14 wherein the set of tines are configured to not penetrate veins.

19. A system according to claim 14 wherein the set of tines are configured to not penetrate arteries.

20. A system for implantation of a medical device in contact with heart tissue, comprising:
- a medical device;
- a set of curved tines mounted to and extending from a distal end of the device, the tines having a length (dD) and an effective cross-sectional area;
- a delivery catheter, enclosing the device and having a distal capsule portion enclosing the tines, the tines exerting a spring force against the capsule and providing a stored potential energy, the delivery catheter having an ejection means for advancing the tines distally from the capsule and fixating the tines within the heart tissue, the ejection means and the stored potential energy of the tines together providing a deployment energy, the tines when so fixated in the tissue providing a fixation energy; and
- wherein the deployment energy provides a maximum peak force of deployment (dDFmax) and the fixation energy provides a maximum peak force of the retraction (dRFmax) and wherein the length of the tines (dD) is such that (dDFmax) and (dRFmax) are equivalent.

21. A system according to claim 20 wherein the device is a medical electrical lead comprising an elongated lead body and wherein the tines are mounted to a distal end of the lead body.

22. A system according to claim 20 wherein the ejection means comprises a pushing means for advancing the lead and tines distally from the capsule.

23. A system according to claim 20 wherein the set of tines are configured to solely penetrate viable tissue.

24. A system according to claim 20 wherein the set of tines are configured to not penetrate veins.

25. A system according to claim 20 wherein the set of tines are configured to not penetrate arteries.

26. A system for implantation of a medical device in contact with heart tissue, comprising:
- a medical device;
- a set of curved tines mounted to and extending from a distal end of the device, the tines having a length (dD) and an effective cross-sectional area;
- a delivery catheter, enclosing the device and having a distal capsule portion enclosing the tines, the tines exerting a spring force against the capsule and providing a stored potential energy, the delivery catheter having an ejection means for advancing the tines distally from the capsule and fixating the tines within the heart tissue, the ejection means and the stored potential energy of the tines together providing a deployment energy, the tines when so fixated in the tissue providing a fixation energy; and
- wherein the potential energy provided by the spring force of the tines against the capsule is less than the fixation energy.

27. A system according to claim 26 wherein the device is a medical electrical lead comprising an elongated lead body and wherein the tines are mounted to a distal end of the lead body.

28. A system according to claim 26 wherein the ejection means comprises a pushing means for advancing the lead and tines distally from the capsule.

29. A system according to claim 26 wherein the set of tines are configured to solely penetrate viable tissue.

30. A system according to claim 26 wherein the set of tines are configured to not penetrate veins.

31. A system according to claim 26 wherein the set of tines are configured to not penetrate arteries.

* * * * *